(12) United States Patent
Ataide Saraiva et al.

(10) Patent No.: US 9,732,091 B2
(45) Date of Patent: Aug. 15, 2017

(54) TRYPTOPHANOL-DERIVED OXAZOLOISOINDOLINONES: SMALL-MOLECULE P53 ACTIVATORS

(71) Applicants: UNIVERSIDADE DO PORTO, Oporto (PT); FACULDADE DE FARMACIA DA UNIVERSIDADE DE LISBOA, Lisbon (PT)

(72) Inventors: Lucilia Helena Ataide Saraiva, Oporto (PT); Maria Manuel Duque Vieira Marques Dos Santos, Lisbon (PT); Nuno Alexandre Lousa Pereira, Lisbon (PT); Clara Isabel Ferreira Pereira, Oporto (PT); Sara Gomes Moreira, Oporto (PT); Mariana Valencia Castanheira Ferreira Leao, Oporto (PT); Angelo Filipe Almeida Monteiro, Lisbon (PT); Joana Oliveira Gama Soares, Oporto (PT)

(73) Assignees: UNIVERSIDADE DO PORTO, Oporto (PT); FACULDADE DE FARMACIA DA UNIVERSIDADE DE LISBOA, Lisbon (PT)

( * ) Notice: Subject to any disclaimer, the term of this patent is extended or adjusted under 35 U.S.C. 154(b) by 0 days.

(21) Appl. No.: 14/901,314

(22) PCT Filed: Jun. 26, 2014

(86) PCT No.: PCT/IB2014/062617
§ 371 (c)(1),
(2) Date: Dec. 28, 2015

(87) PCT Pub. No.: WO2014/207688
PCT Pub. Date: Dec. 31, 2014

(65) Prior Publication Data
US 2016/0347765 A1 Dec. 1, 2016

(30) Foreign Application Priority Data
Jun. 26, 2013 (PT) .................................. 107025

(51) Int. Cl.
*C07D 498/04* (2006.01)
*A61K 31/424* (2006.01)
*A61K 45/06* (2006.01)

(52) U.S. Cl.
CPC .......... *C07D 498/04* (2013.01); *A61K 31/424* (2013.01); *A61K 45/06* (2013.01)

(58) Field of Classification Search
CPC ................................................... C07D 498/04
See application file for complete search history.

(56) References Cited

U.S. PATENT DOCUMENTS 6,958,333 B1 * 10/2005 Hayama ............... C07D 213/75
514/230.2
2004/0198783 A1 10/2004 Garlich et al.

FOREIGN PATENT DOCUMENTS

| EP | 1199306 A1 | 4/2002 |
| WO | 2008005268 A1 | 1/2008 |
| WO | 2010038043 A1 | 4/2010 |
| WO | 2010042445 A1 | 4/2010 |

OTHER PUBLICATIONS

Golub et al., Science, vol. 286, Oct. 15, 1999, pp. 531-537.*
International Search Report dated Oct. 2, 2014 for PCT/IB2014/062617.

* cited by examiner

*Primary Examiner* — Laura L. Stockton
(74) *Attorney, Agent, or Firm* — Lucas & Mercanti, LLP (57) ABSTRACT

The present application discloses novel family of Tryptophanol-Derived Oxazoloisoindolinones for use in the treatment of p53 associated conditions, such as cancer.
These compounds are p53 activators and may be used in pharmaceutical compositions, alone or in combination with other chemotherapeutic agents.

12 Claims, 10 Drawing Sheets

TRYPTOPHANOL-DERIVED OXAZOLOISOINDOLINONES: SMALL-MOLECULE P53 ACTIVATORS

CROSS REFERENCE TO RELATED APPLICATION

This Application is a 371 of PCT/IB2014/062617 filed on Jun. 26, 2014 which, in turn, claimed the priority of Portuguese Patent Application No. 107025 filed on Jun. 26, 2013.

TECHNICAL FIELD

The present invention relates to tryptophanol-derived oxazoloisoindolinones as activators of wild-type and mutant p53 activity.

BACKGROUND

The p53 transcription factor has been considered one of the most appealing targets for developing anticancer treatments. Indeed, the fact that the p53-signaling pathway is inactivated in all types of cancers has drawn great attention from the world-wide cancer researchers to target p53 for the development of improved cancer therapies. Specifically, about 50% of the patients contain various inactivating mutations in p53, while the other 50% possess defective components in posttranslational modification of the p53 protein or abrogation of the p53-signaling pathway by endogenous negative regulators, such as MDM2 and MDMX. The transformed environment of tumor cells appears to be super-responsive to the re-introduction of p53 activity, which turns on the tumor suicidal pathway. Based on this, several small-molecules targeting the p53 pathway have emerged, most of them targeting the p53 interaction with MDM2.

The high prevalence of mutant forms of p53 in human cancers and the often observed increased drug resistance of mutant p53-expressing tumors makes mutant p53 forms highly appealing targets for novel cancer therapies. Additionally, due to its high selectivity for tumor cells, by reactivating the mutant p53, high efficiency combined with minimum side effects can be achieved. Even though the diversity of mutations in tumors, the majority have common features that would make restoring wild-type p53 functions feasible. Most of them are missense mutations in the DNA-binding core domain that results in mutant p53 conformational changes and consequent loss of DNA binding activity. Hence, the search for small-molecules that can stabilize mutant p53 in its active biological conformation by restoring its binding and transcriptional activity will have a profound impact on cancer therapy. Recently, this approach led to the identification of some small-molecules that restore wild-type p53 function to a wide range of p53 mutants (e.g. CP-31398 and PRIMA-1).

Despite the recent identification of some p53 activators, for most of them, the molecular mechanism of action is far from being clear. Additionally, the few described compounds might have unfavorable pharmacokinetics or toxicity profiles and therefore will not be useful. Thus, more potent and selective pharmacological alternatives to the activation of p53 function for neoplastic cells are still largely required, specially avoiding deleterious adverse effects associated with many of the current cancer therapies [reviewed in (Wade et al. Nat. Rev. Cancer 2013, 13, 83-96; Pei et al., Oncotarget 2012, 3, 228-235; Chen et al. Biochem Pharmacol. 2010, 80:724-30; Wiman 2010 Oncogene 29:4245-52; Wang and Sun, Translational Oncology 2010, 3:1-12)].

SUMMARY

The present invention provides a novel family of small-molecule activators of p53, tryptophanol-derived oxazoloisoindolinones of the general formula (I):

Such compounds may be used in pharmaceutical compositions for the treatment of cancers with wt or mutant p53, alone or in combination with other chemotherapeutic agents.

The present application describes a compound or pharmaceutically acceptable salt, ester, solvate or prodrug thereof, of formula (I), wherein:

X is C=O, $CH_2$, CH—OH, C=NOH, C=$NOCH_3$, NO, NOH, S=O or $SO_2$;

$R^1$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, substituted or unsubstituted aryl, substituted or unsubstituted heteroaryl, substituted or unsubstituted aralkyl, or substituted or unsubstituted heteroaralkyl;

$R^2$ to $R^9$ are independently selected from the group consisting of hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, hydroxyl, aldehyde, halogen, trifluoromethyl, amine, carboxyl, cyano, nitro, carbonylmethylsulfone, trifluoromethylsulfone, and substituted or unsubstituted sulfonamide, substituted or unsubstituted aryl, substituted or unsubstituted heteroaryl, substituted or unsubstituted aralkyl, or substituted or unsubstituted heteroaralkyl;

$R^{10}$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkylamine, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl.

A preferred embodiment of the present invention describes the compound comprising one or more asymmetric centers such as enantiomer, diastereomer or other stereoisomeric forms defined in terms of absolute stereochemistry as (R)- or (S)- or as (D)- or (L)-, its tautomer or racemate; or mixture thereof, or pharmaceutically acceptable salt, ester, solvate or prodrug thereof.

In another embodiment of the present invention, at least one of $R^1$ to $R^9$ are, independently of each other, an amine group or aminoalkyl and wherein the compound comprises counterions such as $HCO_3^-$, $CO_3^{2-}$, $Cl^-$, $NH_2C_6H_4SO_3^-$, $1\text{-}CH_3C_6H_2\text{-}3\text{-}OH\text{-}4(CHCH_3)\text{-}6\text{-}SO_3^-$ which are coordinated or ionically bound in the amine or aminoalkyl.

A preferred embodiment of the present invention describes the compound of formula (II)

(II)

In yet another preferred embodiment of the present invention, the compound is of formula (III)

(III)

A preferred embodiment of the present invention describes a pharmaceutical composition comprising a therapeutically effective amount of the compound described above and further comprising a pharmaceutically effective carrier and a chemotherapeutic agent.

In another embodiment of the present invention, the pharmaceutical composition is administered via topical, oral, parenteral or injectable route.

A preferred embodiment of the present invention describes the use of compound described as a p53 activator.

In another embodiment of the present invention, the compound is use in the treatment of a neoplasia, preferably in the treatment of a cancer that is positively influenced by the activation of wild-type or mutant p53 forms.

A preferred embodiment of the present invention describes the use of the compound described as a chemoprotectant.

In another embodiment of the present invention, the pharmaceutical composition described is used as a p53 activator.

In another embodiment of the present invention, the pharmaceutical composition described is used in the treatment of a neoplasia, preferably in the treatment of a cancer that is positively influenced by the activation of wild-type or mutant p53 forms.

In another embodiment of the present invention, the pharmaceutical composition described is used as a chemoprotectant.

General Description

The present invention provides a new family of small-molecule activators of wild-type (wt) and mutant p53 forms, tryptophanol-derived oxazoloisoindolinones of the general formula (I) their salts or esters, wherein:

X is C=O, $CH_2$, CH—OH, C=NOH, C=NOCH$_3$, NO, NOH, S=O or $SO_2$;

$R^1$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, substituted or unsubstituted aryl, substituted or unsubstituted heteroaryl, substituted or unsubstituted aralkyl, or substituted or unsubstituted heteroaralkyl;

$R^2$-$R^9$
are, independently of each other, hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, hydroxyl, aldehyde, halogen, trifluoromethyl, amine, carboxyl, cyano, nitro, carbonylmethylsulfone, trifluoromethylsulfone, and substituted or unsubstituted sulfonamide, substituted or unsubstituted aryl, substituted or unsubstituted heteroaryl, substituted or unsubstituted aralkyl, or substituted or unsubstituted heteroaralkyl;

wherein if one of $R^2$-$R^9$ is an amine group and/or aminoalkyl this contains counterions such as $HCO_3^-$, $CO_3^{2-}$, $Cl^-$, $NH_2C_6H_4SO_3^-$, $1\text{-}CH_3C_6H_2\text{-}3\text{-}OH\text{-}4(CHCH_3)\text{-}6\text{-}SO_3^-$ which are coordinated or ionically bound in the amine;

$R^{10}$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkylamine, substituted or unsubstituted alkenyl, substituted or unsubstituted alkynyl, substituted or unsubstituted aryl, substituted or unsubstituted heteroaryl, substituted or unsubstituted aralkyl, and substituted or unsubstituted heteroaralkyl;

The term "halogen" is used herein to denote a halogen atom which is typically selected from fluorine, chlorine, bromine or iodine.

The term "alkyl" is used herein to denote, in particular, a lower alkyl group, branched (including ring structures formed via the linking of two branches at the same carbon atom) or straight chain hydrocarbon having one to eight carbon atoms, for example propyl.

The term "cycloalkyl" are defined herein as non-aromatic saturated hydrocarbons having at least one carbon-atom ring (typically having from 6 to 10 ring carbon atoms), for example cyclohexyl or cyclooctyl.

The term "alkenyl" is used herein to denote an alkyl group including one or more carbon-carbon double bonds, for example propenyl or cyclopentenyl.

The term "alkynyl" is used herein to denote an alkyl group including one or more carbon-carbon triple bonds, for example propynyl.

The term "aryl" is used herein to denote a carbocyclic group or structure having at least one aromatic ring. The said ring may form part of a multiple condensed ring structure, for example phenyl, naphthalene or anthracene.

The term "aralkyl" is used herein to denote an alkyl chain in which there is an aryl group attached thereto, for example benzyl.

The term "heteroaryl" is used herein to denote an aryl group in which said group comprises at least one heteroatom, selected from, for example N, O or S. Examples of heteroaryl groups which may be used in accordance with the invention include, but are not limited to, pyridine, pyrrole, furan, thiophene and imidazole.

The term "heteroaralkyl" is used herein to denote an aralkyl substituent in which at least one aromatic ring comprises at least one heteroatom selected from, for example N, O or S. Examples of heteroaralkyl groups which may be used in accordance with the invention include, but are not limited to, methylpyridine and methylfuran.

The term "substituted alkyl" is used herein to denote an alkyl substituent which is substituted with one or more functional groups.

The term "substituted alkenyl" is used herein to denote an alkenyl substituent which is substituted with one or more functional groups.

The term "substituted alkynyl" is used herein to denote an alkynyl substituent which is substituted with one or more functional groups.

The term "substituted aryl" is used herein to denote an aryl substituent which is substituted with one or more functional groups. Examples of substituted aryl groups which may be used in accordance with the invention include, but are not limited to, halophenyl, nitrophenyl, methylphenyl, or cyanophenyl.

The term "substituted heteroaryl" is used herein to denote a heteroaryl substituent which is substituted with one or more functional groups.

The term "substituted aralkyl" is used herein to denote an aralkyl substituent which is substituted with one or more functional groups. Examples of substituted aralkyl groups which may be used in accordance with the invention include, but are not limited to, halobenzyl, acetylbenzyl, benzonitrile, methoxybenzyl, carboxamidobenzyl, benzoylbenzyl, nitrobenzyl, cyanobenzyl, or methylbenzyl.

The term "substituted heteroaralkyl" is used herein to denote a heteroaralkyl substituent which is substituted with one or more functional groups.

The term "alkoxy" is used herein to denote an alkyl group which is linked to a second chemical structure, which may be any of the foregoing, by way of an oxygen atom. The carbon chain of the alkyl group may be substituted with one or more functional groups to provide a "substituted alkoxy". Examples of alkoxy groups which may be used in accordance with the invention include, but are not limited to, methoxy, ethoxy, and propoxy.

The term "alkylamine" is used herein to denote an alkyl group comprising at least one amine function. The carbon chain of the alkyl group may be substituted with one or more functional groups. The amine function may be primary, secondary or tertiary. Examples of alkylamine groups which may be used in accordance with the invention include, but are not limited to, ethylamine and butylamine. The amine function may form part of a cyclic or heteroaromatic structure or another functionality, for example amide.

As referred to herein suitable functional groups for substitution as described above include, but are not limited to, any of the following which may be used alone or in combination: halo, hydroxyl, hydroxyalkyl, alkoxy, acyl, acetamide, carboxyl, cyano, carboxamide, sulfonamide, sulfone, sulfoxide, amino, or silico ligand.

The compounds of this invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for aminoacids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved conventional techniques.

Compounds used in the present invention are prepared according to the following general reaction sequences.

General Reaction Scheme (Enantioselective Synthesis of Tryptophanol-Derived Oxazoloisoindolinones from Reaction of Chiral Tryptophanol and Oxoacids):

A formulation or pharmaceutical composition containing these compounds as effective components, together with pharmaceutically effective carriers, may be used in the treatment of cancers with wt or mutant p53, after further pre-clinic studies.

BRIEF DESCRIPTION OF DRAWINGS

Without intent to limit the disclosure herein, this application presents attached drawings of illustrated embodiments for an easier understanding.

FIG. 1 illustrates that SLMP53-1 and SLMP53-2 increase the p53 effects in yeast. Yeast cells expressing human wt p53 and transformed with the empty vector (control yeast) were incubated in selective induction medium in the presence of 0.1-25 μM compound or DMSO only, for 42 hours. (A) Effect of 10 μM SLMP53-1 and SLMP53-2 on the p53-induced yeast growth inhibition. Results are plotted setting as one unit the p53-induced growth inhibition in the presence of DMSO only. Growth was estimated by colony-forming unit (CFU) counts. Data are mean±S.E.M. of five independent experiments; values significantly different from DMSO only (**$P<0.01$; unpaired Student's t-test). (B) Dose-response curve for SLMP53-1 in yeast cells expressing human p53 and control yeast. Cells were incubated in selective medium with 0.1-25 μM of SLMP53-1 or DMSO only. Results are plotted setting as 100% growth inhibition the number of CFU obtained in the presence of DMSO only. Data are mean±S.E.M. of three independent experiments (*$P<0.05$; unpaired Student's t-test). (C) Effect of SLMP53-1 and SLMP53-2 on p53-induced S-phase cell cycle arrest in yeast. Cell cycle phases were analyzed by flow cytometry using Sytox Green and quantified using ModFit LT software; quantification of cell cycle phases represent the mean values. (D) Increase of p53-induced actin protein expression levels by SLMP53-1 and SLMP53-2 in yeast expressing p53. Western Blot band intensity was quantified using Pgk1p as loading control (with Bio-Profile Bio-1D++ software).

FIG. 3 illustrates the effect of SLMP53-1 on cell cycle progression of HCT116 $p53^{+/+}$ cells. Cell cycle phases were analyzed by flow cytometry using propidium iodide and quantified using ModFit LT software (Verity Software House Inc., Topsham, USA). Effect of compounds (double $GI_{50}$) was analyzed after 24 hours treatment. Histograms represent one of two independent experiments; quantification of cell cycle phases represents the mean±S.E.M. of two independent experiments. Values significantly different from DMSO (*$P<0.05$; unpaired Student's t-test).

FIG. 4 illustrates that SLMP53-1 induces early and late apoptosis in HCT116 $p53^{+/+}$ cells. Apoptosis was analyzed by flow cytometry using FITC-Annexin V and propidium iodide. The effect of compounds was analyzed after 24 hours treatment using the concentration of $GI_{50}$ and double $GI_{50}$. Histograms represent one of two independent experiments; quantification of cells in apoptosis represents the mean±S.E.M. of two independent experiments. Values significantly different from DMSO only (*$P<0.05$; unpaired Student's t-test).

FIG. 6 illustrates that SLMP53-1 reactivates mutant p53s R273H, R175H and R280K in yeast. Yeast cells expressing R273H, R280K, Y220C or R175H were incubated in selective medium with 10 μM of SLMP53-1, 10 μM of CP-31398 (for R273H), 10 μM of PRIMA-1 (for R175H and R280K), 50 μM of PhiKan 083 (for Y220C) or DMSO only, for 44 hours. CP-31398, PRIMA-1 and PhiKan 083 were used as positive controls. Results are plotted setting as 100% growth the number of CFU obtained in the presence of DMSO only. Data are mean±S.E.M. of four independent experiments; values significantly different from yeast incubated with DMSO only (*$P<0.05$; unpaired Student's t-test).

FIG. 8 illustrates that SLMP53-1 induces late apoptosis in MDA-MB-231 cells. Apoptosis was analyzed by flow cytometry using FITC-Annexin V and propidium iodide. The effect of compounds was analyzed after 24 hours treatment using the concentration of $GI_{50}$. Histograms represent one of two independent experiments; quantification of cells in apoptosis represents the mean±S.E.M. of two independent experiments. Values significantly different from DMSO only (*$P<0.05$ and ** $P<0.01$; unpaired Student's t-test).

FIG. 10 illustrates the antitumor activity of SLMP53-1 in vivo. BALB/c mice, 4-6 weeks old, were implanted subcutaneous xenografts using $1.5 \times 10^6$ HCT116 $p53^{+/+}$ or HCT116 $p53^{-/-}$ cells. The treatment was initiated when palpable tumors were established (14 days after the cells were injected), and consisted in 4 intraperitoneal injections (2× per week) of vehicle (control) or 50 mg/kg of SLMP53-1. Xenografts were measured during 24 days. Relative tumor volumes were plotted for control and treated groups by dividing the average tumor volume for each data point by average starting tumor volume.

DESCRIPTION OF THE EMBODIMENTS

Referring to the drawings, herein are described optional embodiments in more detail, which however are not intended to limit the scope of the present application.

Experimental Procedure for the Preparation of Tryptophanol-Derived Oxazoloisoindolinones In a preferred embodiment, the tryptophanol-derived oxazoloisoindolinones are prepared according to the following method:

To a stirred solution of tryptophanol (0.842 mmol, 1.0 eq.) in 15 mL of toluene, under reflux in a Dean-Stark apparatus, was added 2-acetyl-benzoic Acid. The reaction was kept under reflux until total consumption of the starting material. The solvent was evaporated and the residue obtained was purified by flash chromatography (Ethyl Acetate/n-Hexane 3:7), followed by recrystallization in EtOAc/n-Hexane.

SLMP53-1, Formula (II), was obtained starting from (S)-tryptophanol in 75% (0.2 g) as a white solid. $^1$H NMR (400 MHz, DMSO) δ 10.92 (s, 1H, NH), 7.74-7.65 (m, 3H, H—Ar), 7.59 (m, 2H, H—Ar), 7.40-7.32 (m, 2H, H—Ar), 7.08 (t, J=7.1 Hz, 1H, H—Ar), 7.01 (t, J=7.4 Hz, 1H, H—Ar), 4.43-4.27 (m, 2H, CH e $OCH_2$), 4.14 (dd, J=8.0, 6.1 Hz, 1H, $OCH_2$), 3.25 (dd, J=14.5, 5.1 Hz, 1H, $CH_2$), 3.12 (dd, J=14.6, 8.1 Hz, 1H, $CH_2$), 1.67 (s, 3H, $CH_3$); 13C NMR (101 MHz, DMSO) δ 173.76 (C=O), 147.55 (Cq), 136.63 (Cq), 133.93 (CH—Ar), 131.40 (Cq), 130.81 (CH—Ar), 127.85 (Cq), 124.04 (CH—Ar), 123.87 (CH—Ar), 123.25 (CH—Ar), 121.49 (CH—Ar), 118.86 (CH—Ar), 118.70 (CH—Ar), 111.88 (CH—Ar), 110.60 (Cq), 98.87 (Cq), 74.65 ($OCH_2$), 55.95 (CH), 30.84 ($CH_2$), 22.79 ($CH_3$); $[\alpha]^{20}_D$ +23.7 (c 0.43 g/100 ml, $CH_2Cl_2$).

(II)

SLMP53-2, Formula (III), was obtained starting from (R)-tryptophanol in 76% (0.13 g) as a white solid; $[\alpha]^{20}_D$ −27.1 (c 0.43 g/100 ml, $CH_2Cl_2$). $^1$H and $^{13}$C NMR spectras were found to be identical to the ones obtained for compound SLMP53-1.

(III)

Biological Assays

SLMP53-1 and SLMP53-2 Behaved as Potential Activators of wt p53 in Yeast

Figure 1:
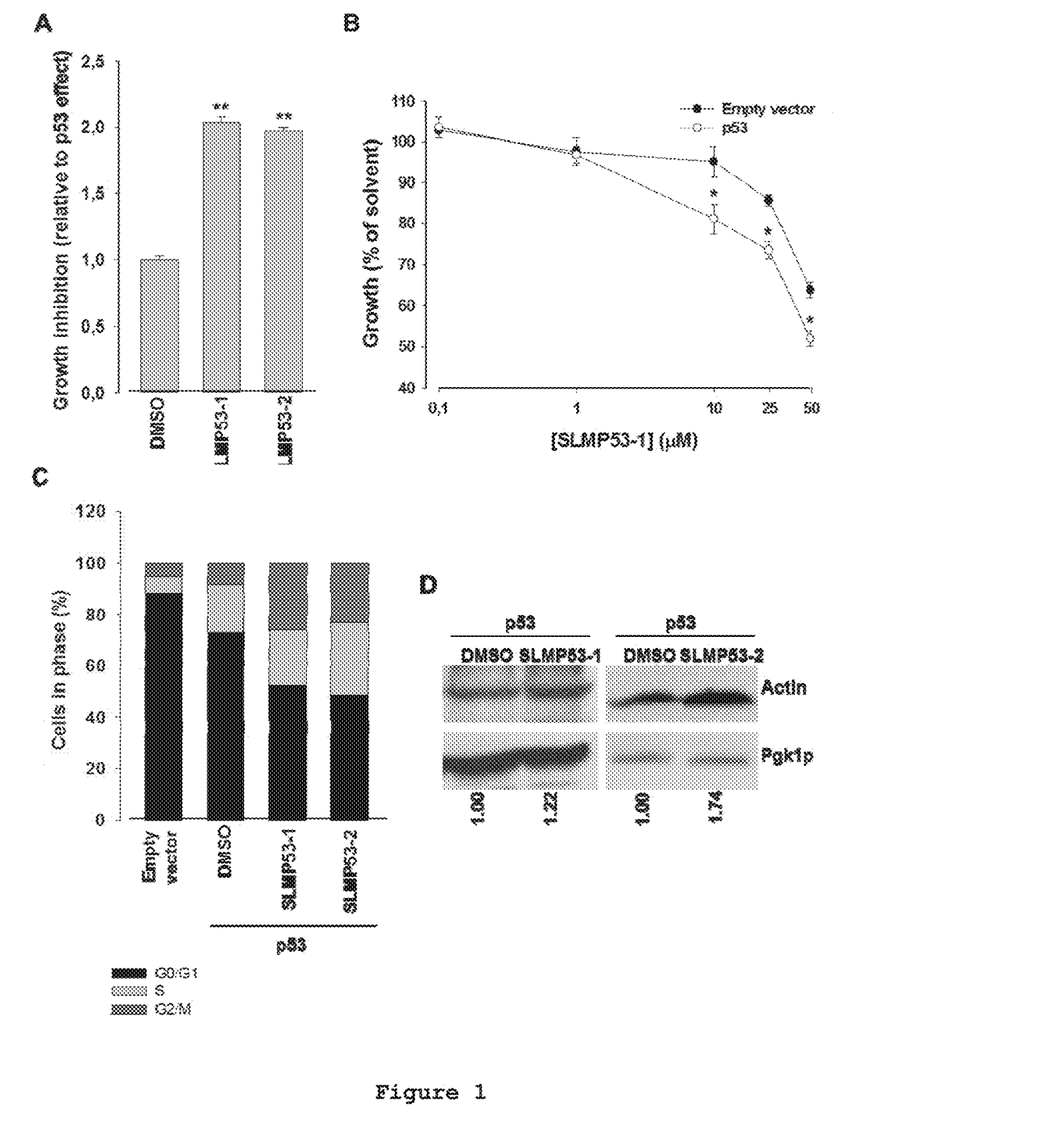
Figure 2:
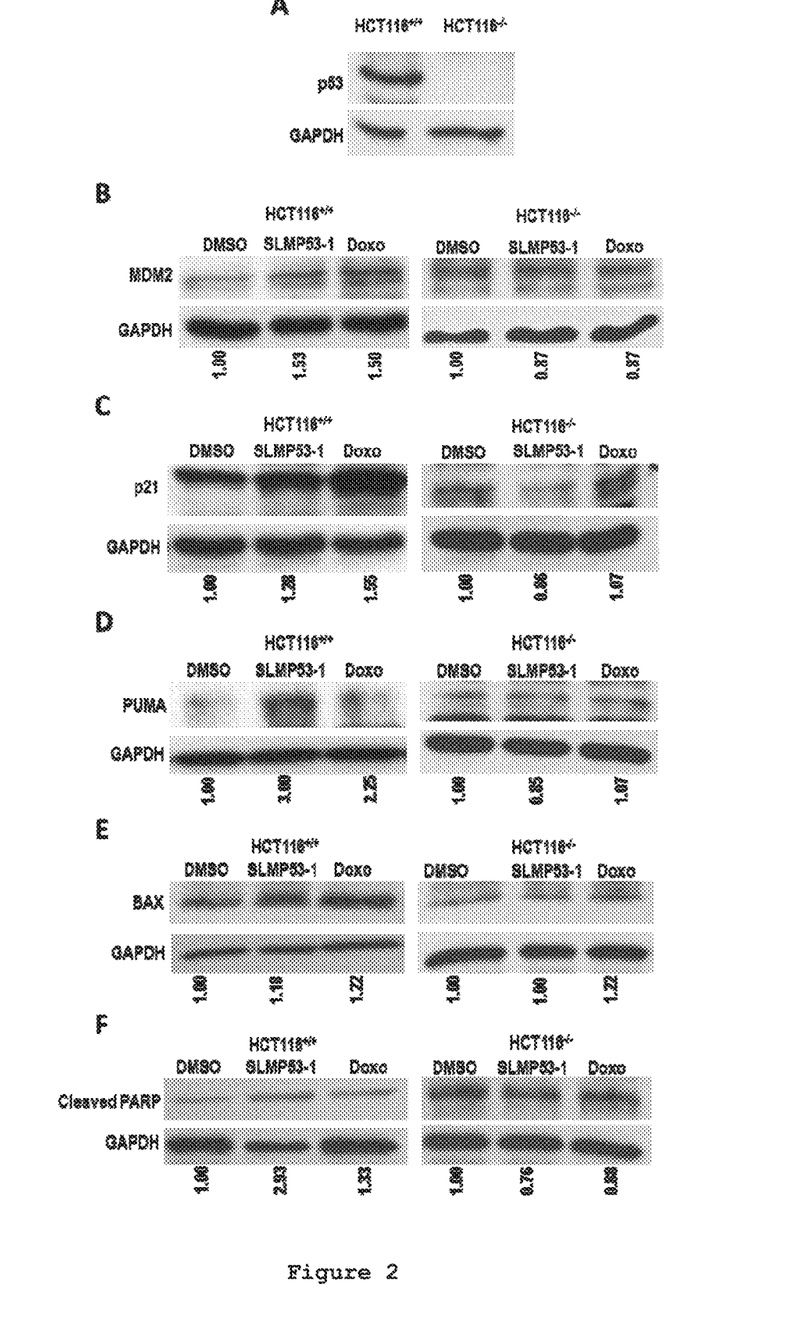
FIG. 2 illustrates that SLMP53-1 increases the levels of proteins encoded by p53 target genes (MDM2, p21, PUMA and BAX), and leads to PARP cleavage in colon carcinoma cells with wt p53 (HCT116 $p53^{+/+}$), but not in colon carcinoma cells without wt p53 (HCT116 $p53^{-/-}$). Western blot analysis was performed for human colon carcinoma cells after 16 (B, D, E) and 24 (A, C, F) hours treatment with 15.5 μM of SLMP53-1, 135 nM doxorubicin (DOXO; positive control) or DMSO only. The protein expression levels were evaluated by quantification of Western Blot band intensity (with Bio-Profile Bio-1D++ software) using GAPDH as loading control.

Using a yeast-based screening approach, the chiral compounds SLMP53-1 and SLMP53-2 were identified as potential activators of wt p53, from a chemical library of tryptophanol-derived oxazoloisoindolinones with general formula (I) shown in FIG. 1, wherein X, $R^1$, $R^2$, $R^3$, $R^4$, $R^5$, $R^6$, $R^7$, $R^8$, $R^9$ and $R^{10}$ are as defined herein, as well as their stereoisomers, enantiomers, ra.cemates, tautomers thereof or mixtures thereof; or a pharmaceutically acceptable salt, solvate or prodrug thereof. In the yeast cell model, compounds SLMP53-1 and SLMP53-2 increased the previously reported (Coutinho et al. FEBS Lett. 2009, 583, 3582-3588) p53-induced growth inhibition (FIGS. 1A and B) and S-phase cell cycle arrest (FIG. 1C). Additionally, the compounds increased the actin protein levels (ACT1 was recently identified as a p53 target gene in yeast; Leão et al. FEBS J. 2013, 280, 6498-507), when compared to yeast cells expressing p53 incubated with DMSO only (FIG. 1D).

SLMP53-1 Had a p53-Dependent Antiproliferative Effect in Colon Carcinoma Tumor Cells The activity of SLMP53-1 as wt p53 activator was further confirmed in colon carcinoma tumor cells with (HCT116 $p53^{+/+}$) and without (HCT116 $p53^{-/-}$) p53 (Table 1). Similarly to the known p53 activator CP-31398, used as positive control, SLMP53-1 exhibited a p53-dependent anti-proliferative effect. In fact, as CP-31398, the $GI_{50}$ (growth inhibition of 50%) value obtained with SLMP53-1 in HCT116 $p53^{+/+}$ cells was 2-fold lower than that obtained in HCT116 $p53^{-/-}$ cells. The effect of PRIMA-I, a known activator of mutant p53 forms, was also evaluated in these tumor cells. Although PRIMA-I presented a similar $GI_{50}$ value to that of SLMP53-1 in HCT116 $p53^{+/+}$ cells, its anti-proliferative effect showed to be p53-independent since a similar $GI_{50}$ value was obtained in the absence of p53 (HCT116 $p53^{-/-}$).

TABLE 1

GI$_{50}$ values obtained for SLMP53-1, CP-31398 and PRIMA-1 in colon carcinoma tumor cells with (HCT116 p53$^{+/+}$) and without (HCT116 p53$^{-/-}$) p53.

| | GI$_{50}$ (µM) | |
|---|---|---|
| | HCT116 p53$^{+/+}$ | HCT116 p53$^{-/-}$ |
| SLMP53-1 | 15.5 ± 1.6 | 34.0 ± 3.5** |
| CP-31398 | 3.4 ± 0.1 | 7.3 ± 0.6** |
| PRIMA-1 | 19.9 ± 4.0 | 13.1 ± 2.0 |

Tumor cells were plated at 5.0×10$^3$ cells/well in 96-well plates and incubated for 24 hours. Cells were then exposed to serial dilutions of SLMP53-1, CP-31398 or PRIMA-1 (from 1.85 to 150 µM). The effect of the compounds was analyzed following 48 hours incubation, using the sulforhodamine B (SRB) assay. The solvent DMSO corresponding to the maximum concentration used in these assays (0.025%) was included as control. The GI$_{50}$ value, the concentration of compound that causes 50% growth inhibition, was calculated for the tested compounds. Results are the mean±S.E.M. of three independent experiments. Value significantly different from HCT116 p53$^{+/+}$ (**P<0.01; unpaired Student's t-test).

SLMP53-1 Increased the Expression Levels of p53 and of Proteins Encoded by p53-Target Genes in HCT116 p53$^{+/+}$ Cells Additionally, it was shown that 15.5 M (GI$_{50}$) of SLMP53-1 increased the protein levels of p53, as well as of proteins encoded by p53-target genes, particularly MDM2, p21, PUMA and BAX in colon carcinoma cells with wt p53 (HCT116 p53$^{+/+}$) (FIG. 2A-E). In these cells, SLMP53-1 also led to PARP cleavage, indicating the stimulation of an apoptotic pathway (FIG. 2F). Contrary to that obtained in HCT116 p53$^{+/+}$, 15.5 µM of SLMP53-1 did not interfere with the expression levels of MDM2, p21, PUMA and Bax, and did not induce PARP cleavage in colon carcinoma cells without p53 (HCT116 p53$^{-/-}$). These results further support the induction of a p53-dependent effect by SLMP53-1 in colon carcinoma cells.

SLMP53-1 Induced Cell Cycle Arrest and Apoptosis in HCT116 p53$^{+/+}$ Cells

Figure 3:
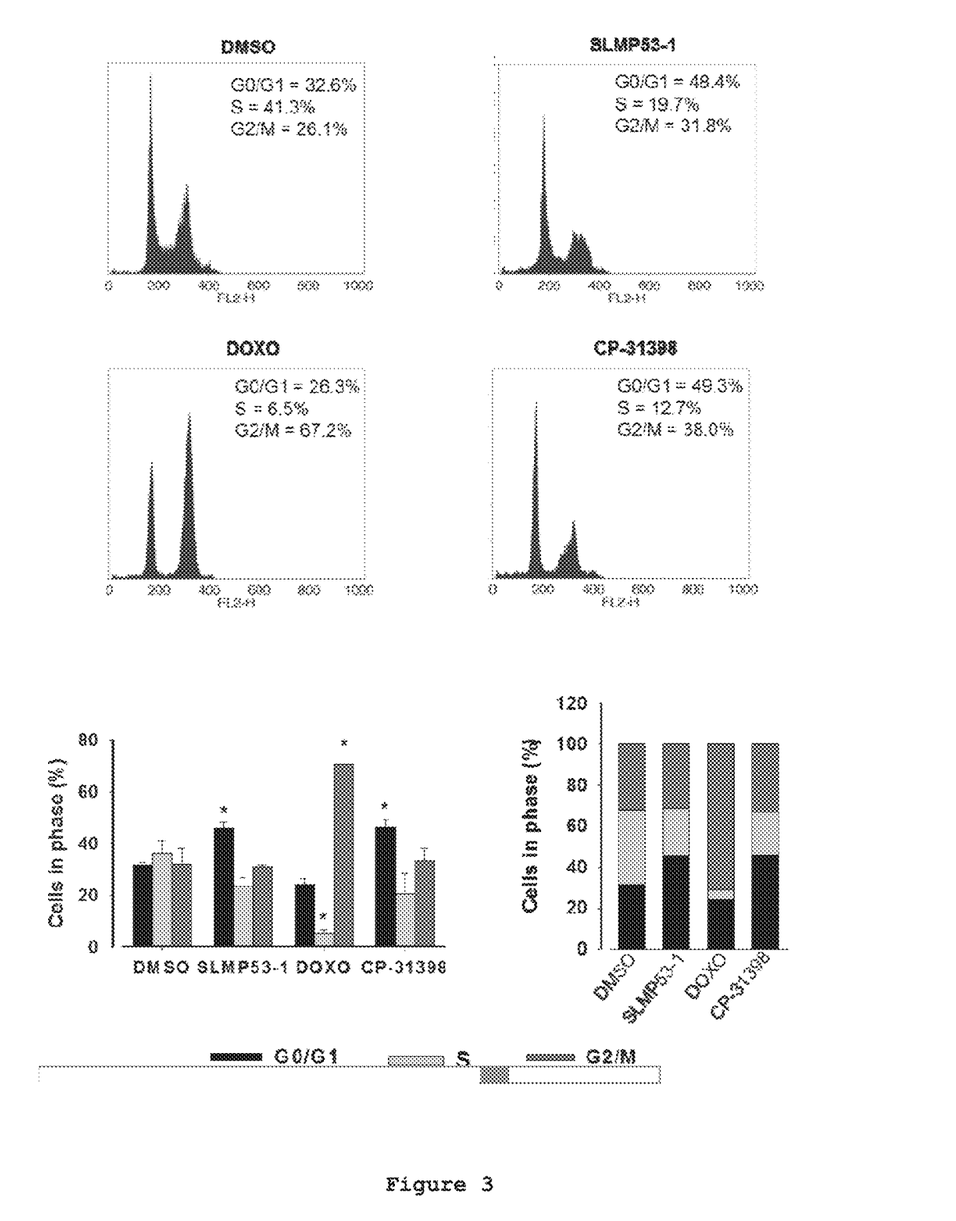
Figure 4:
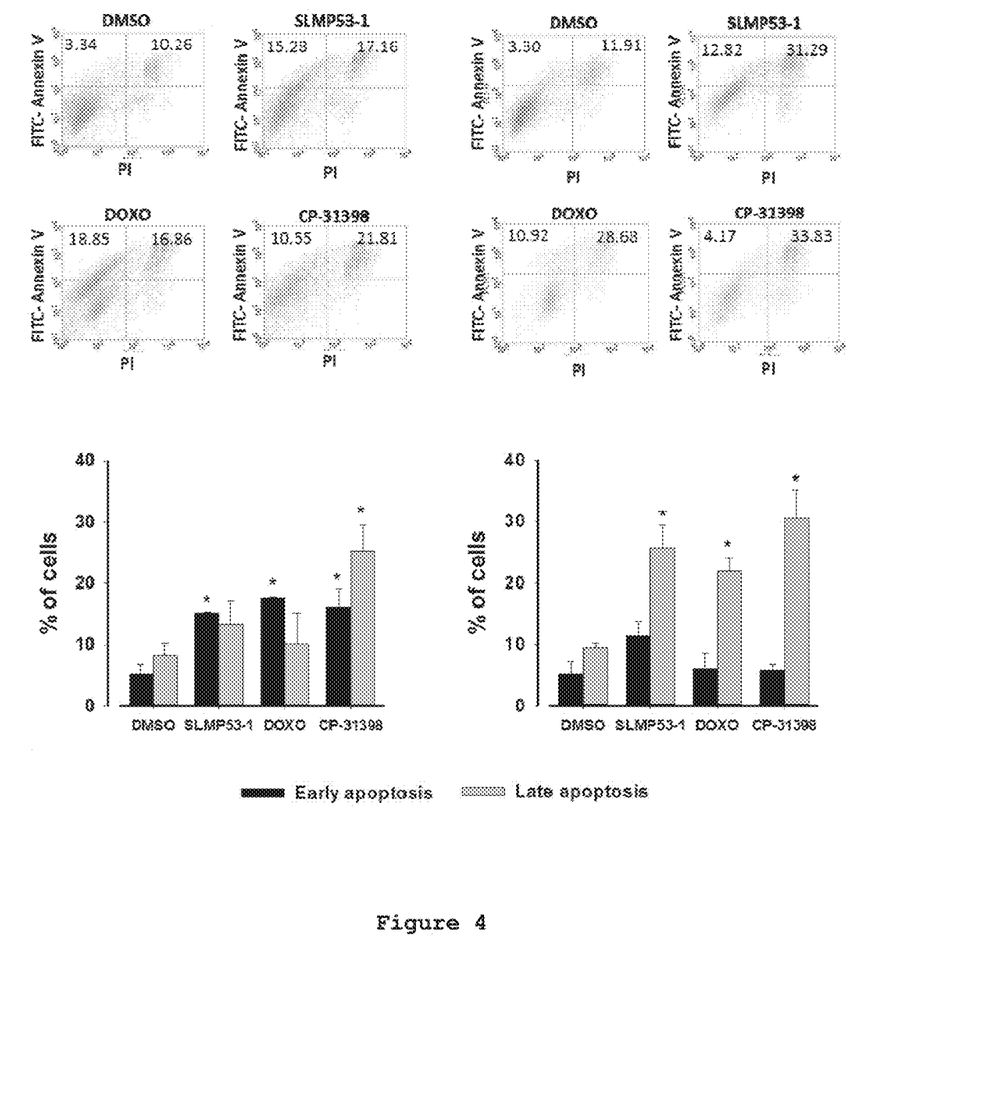

Moreover, it was shown that, similarly to CP-31398, the anti-proliferative effect of SLMP53-1 was associated to the induction of a G0/G1-phase cell arrest (FIG. 3), and of an apoptotic cell death (FIG. 4).

Figure 5:
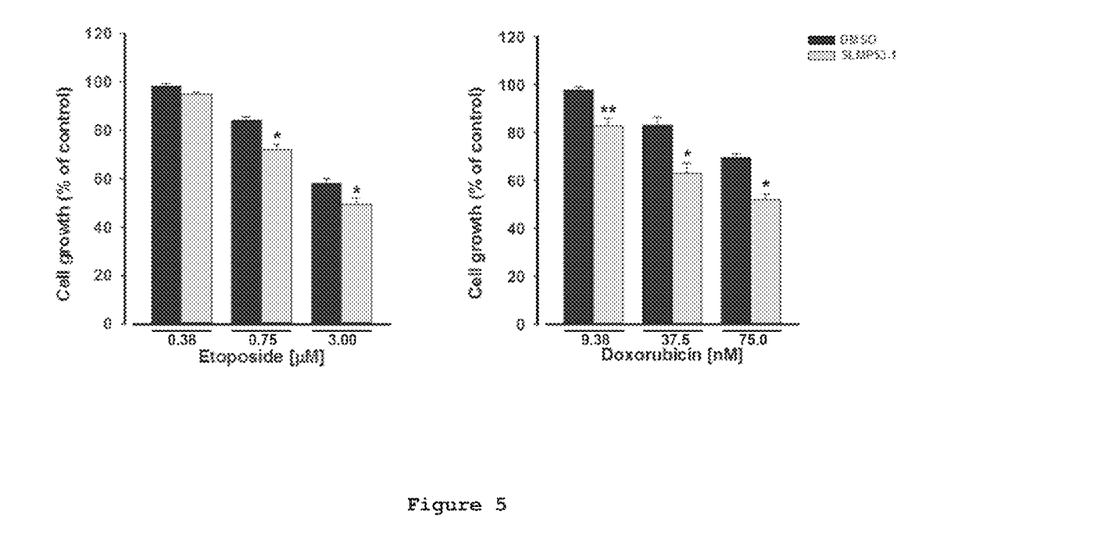
FIG. 5 illustrates that SLMP53-1 sensitizes colon carcinoma tumor cells with wt p53 (HCT116 $p53^{+/+}$) to the effects of etoposide and doxorubicin. HCT116 $p53^{+/+}$ cells were treated for 48 hours with increasing concentrations of etoposide (0.38 to 3.00 μM) or doxorubicin (9.38 to 75.0 nM) in the presence of a very low concentration (between $GI_5$ to $GI_{10}$; 4 μM) of SLMP53-1 or DMSO only. The effect of the compounds on cell growth was analyzed following 48 hours incubation, using the sulforhodamine B (SRB) assay. Results are mean±SEM of three to four independent experiments. Values significantly different from cells incubated with etoposide or doxorubicin only: *$P<0.05$ and **$P<0.01$, unpaired Student's t-test.

SLMP53-1 Sensitized Colon Carcinoma Tumor Cells with Wt p53 (HCT116 p53$^{+/+}$) to the Effects of Etoposide and Doxorubicin It was also investigated if SLMP53-1 increased the sensitivity of HCT116 p53$^{+/+}$ cells to the effects of various concentrations of the conventional chemotherapeutic drugs, etoposide (0.38 to 3.00 µM) and doxorubicin (9.38 to 75 nM). For that, a low concentration of SLMP53-1 (approximately the GI$_5$ to GI$_{10}$ concentration; 4 µM; without significant anti-proliferative effect on tumor cells) was used. The results showed that SLMP53-1 increased the etoposide/doxorubicin-induced growth inhibition in HCT116 p53$^{+/+}$ tumor cells at two etoposide concentrations tested (0.75 and 3.00 µM) and at three doxorubicin concentrations tested (9.38, 37.5 and 75 nM) (FIG. 5). Interestingly, for 9.38 nM doxorubicin (for which an anti-proliferative effect is not observed), a 15% decrease of tumor cell growth was obtained in the presence of 4 µM of SLMP53-1.

SLMP53-1 Reactivated Some Forms of Mutant p53 in Yeast

Figure 6:
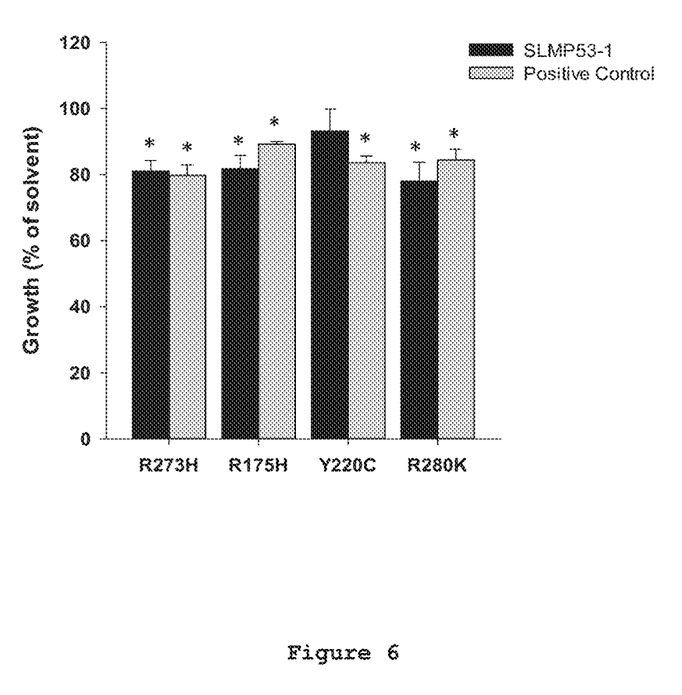

It is also shown that SLMP53-1 can reactivate some mutant p53 forms, particularly R273H, R280K and R175H (FIG. 6). In opposition to wt p53, these mutant p53 forms do not induce a significant yeast growth inhibition. However, when treated with 10 µM of SLMP53-1 a significant growth inhibition (similar to that obtained with wt p53) was obtained.

Anti-Proliferative Effect of SLMP53-1 in Human Tumor Cells Harboring a Mutant p53:

Based on the results obtained in yeast, the anti-proliferative effect of SLMP53-1 was studied in human tumor cells harboring one of the mutant p53 forms (R280K) reactivated by SLMP53-1 in yeast, namely the human breast cancer MDA-MB-231 cell line (Table 2). The results obtained showed that SLMP53-1 had a potent anti-proliferative effect on MDA-MB-231 cell lines with the mutant p53 R280K. In this tumor cell line, SLMP53-1 presented a lower potency than CP-31398, but was more potent than PRIMA-1. These results therefore indicated that for tumor cells with the mutant p53 R280K, SLMP53-1 may represent a suitable pharmacological alternative to PRIMA-1. In spite of the higher potency exhibited by CP-31398 in this tumor cell line compared to SLMP53-1, cytotoxic and genotoxic effects have been reported for this compound (Rippin et al. Oncogene 2002, 21, 2119-2129; Jonhson et al. Toxicology 2011, 289, 141-150). The therapeutic applicability of CP-31398 as an anticancer compound has been therefore questioned, as well as its molecular mechanism of action as p53 activator.

TABLE 2

GI$_{50}$ values obtained for SLMP53-1, CP-31398 and PRIMA-1 in breast cancer MDA-MB-231 cells with the mutant p53 R280K.

| | GI$_{50}$ (µM)<br>MDA-MB-231<br>(p53R280K) |
|---|---|
| SLMP53-1 | 16.6 ± 4.2 |
| CP-31398 | 2.3 ± 0.9 |
| PRIMA-1 | 29.8 ± 3.1 |

Tumor cells were plated at 7.5×10$^3$ cells/well in 96-well plates and incubated for 24 hours. Cells were then exposed to serial dilutions of SLMP53-1, CP-31398 or PRIMA-1 (from 1.85 to 150 µM). The effect of the compounds was analyzed following 48 hours incubation period, using the sulforhodamine B (SRB) assay. The solvent DMSO corresponding to the maximum concentration used in these assays (0.025%) was included as control. The GI$_{50}$ value, which is the concentration of compound that causes 50% growth inhibition, was calculated for the tested compounds. Results are the mean±S.E.M. of three independent experiments.

Figure 7:
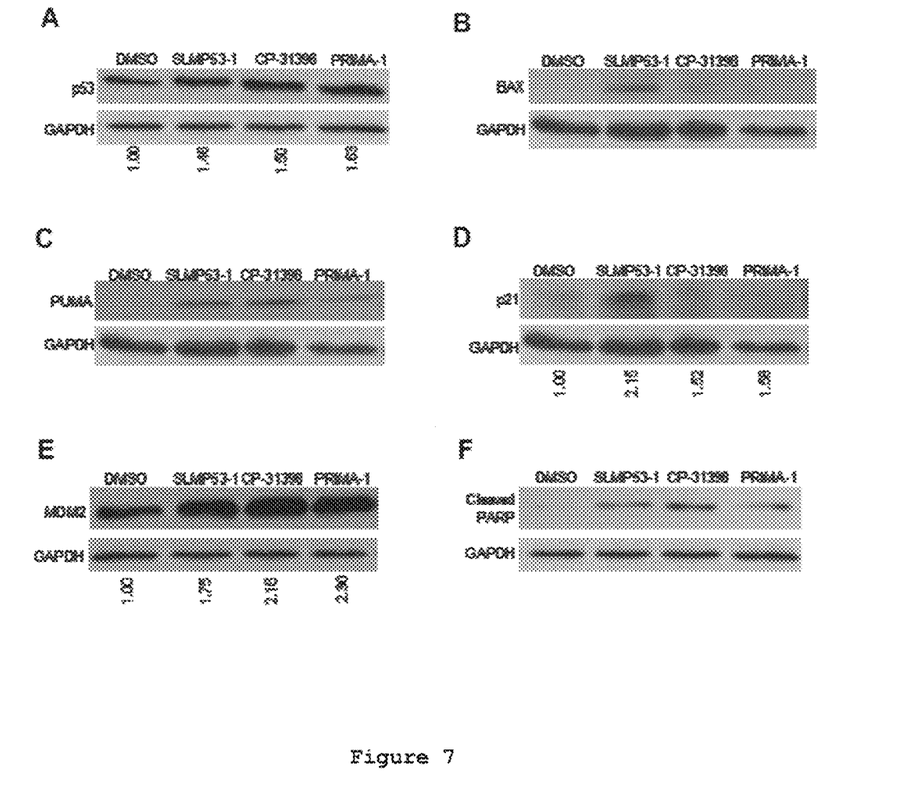
FIG. 7 illustrates that SLMP53-1 increases the levels of p53 and of proteins encoded by p53-target genes in MDA-MB-231 breast tumor cells. Western blot analysis was obtained for MDA-MB-231 breast tumor cells after treatment with the $GI_{50}$ concentration: 16.6 μM SLMP53-1, 2.3 μM CP-31398, 29.8 μM PRIMA-1 or DMSO only, for 24 hours in A, B, D and E; and for 48 hours in C and F. The protein levels were evaluated by quantification of Western Blot band intensity (with Bio-Profil Bio-1D++ software) using GAPDH as loading control.

SLMP53-1 Increased the Expression Levels of p53 and of Proteins Encoded by p53-Target Genes in MDA-MB-231 Cells It was observed that 16.6 µM (GI$_{50}$) of SLMP53-1 increased the levels of p53 and of proteins encoded by p53-target genes as BAX, PUMA and p21, and lead to PARP cleavage in MDA-MB-231 tumor cells evaluated after 24/48 hours treatment by Western blot analysis (FIG. 7).

SLMP53-1 Induced Apoptosis in MDA-MB-231 Cells

Figure 8:
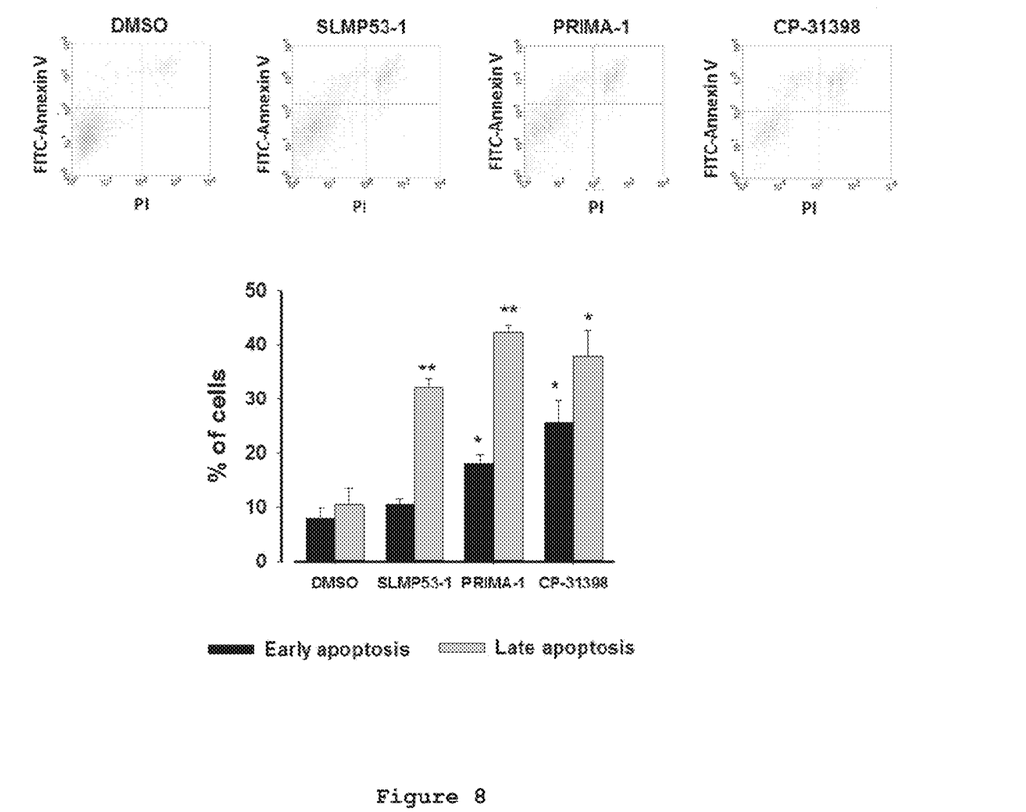

Moreover, it was shown that, like CP-31398 and PRIMA-1, the anti-proliferative effect of SLMP53-1 was associated with an apoptotic cell death (FIG. 8).

Figure 9:
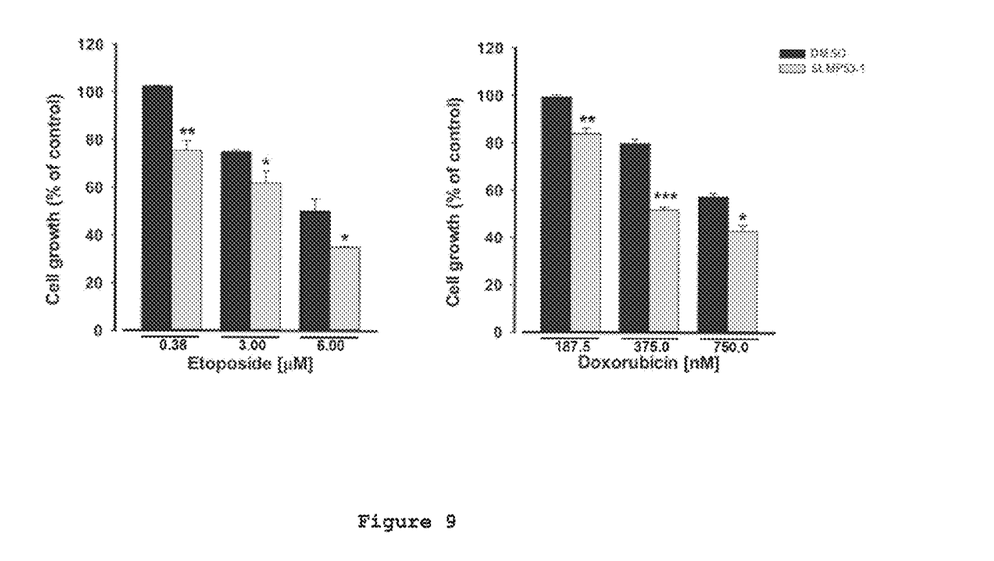
FIG. 9 illustrates that SLMP53-1 sensitizes breast cancer MDA-MB-231 cells to the effects of etoposide and doxorubicin. The MDA-MB-231 tumor cells (with the mutant p53 R280K) were treated for 48 hours with increasing concentrations of etoposide (0.30 to 6.00 μM) or doxorubicin (187.5 to 750.0 nM) in the presence of a very low concentration (between $GI_5$ to $GI_{10}$; 4 μM) of SLMP53-1 or with DMSO only. Effect of compounds on cell growth was analyzed following 48 hours incubation, using the sulforhodamine B (SRB) assay. Results are mean±SEM of three to four independent experiments. Values significantly different from cells incubated with etoposide or doxorubicin only: *P<0.05, P<0.01 and *P<0.001, unpaired Student's t-test.
Figure 10:
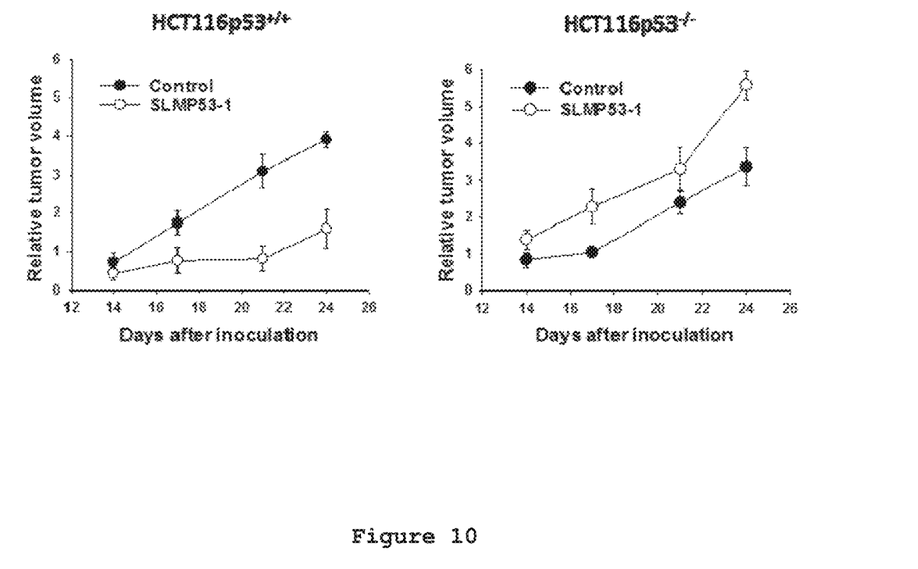

SLMP53-1 Sensitized Breast Cancer MDA-MB-231 Cells with Mutant p53 R280K to the Effects of Etoposide and Doxorubicin:

It was also investigated if SLMP53-1 increased the sensitivity of MDA-MB-231 cells to the effects of various concentrations of etoposide (0.38 to 6.00 μM) and doxorubicin (187.5 to 750.0 nM). For that, a low concentration of SLMP53-1 (approximately the $GI_5$ to $GI_{10}$ concentration; 4 μM; without significant anti-proliferative effects on tumor cell lines) was used. The results showed that SLMP53-1 increased the etoposide/doxorubicin-induced growth inhibition for the three concentrations tested (FIG. 9). Particularly, for 0.38 μM etoposide (for which an anti-proliferative effect is not observed), a 25% decrease of tumor cell growth was obtained in the presence of 4 μM of SLMP53-1.

SLMP53-1 had No Genotoxic Effects Upon Human Lymphocytes Cells

Additionally, favorable apparent permeability coefficients were obtained and no cytotoxic and genotoxic effects were observed for SLMP53-1. Concerning the genotoxicity assays, three concentrations (15.5, 7.25 and 1.55 μM) of SLMP53-1 were tested, in vitro, for potential genotoxicity to human lymphocytes. For that purpose, the cytokinesis-block micronucleus assay (an assay routinely used in mutagen/carcinogen screening programs) was used, which measures the ability of genotoxic agents to induce both chromosomal damage (clastogenic) and/or spindle dysfunction (aneugenic) effects. The results obtained showed that SLMP53-1 does not possess mutagenic potential at the studied concentrations, since differences in micronuclei frequency were not observed, when compared to the negative control. Indeed, since the micronucleus frequency induced by different concentrations was essentially constant, this suggests that the absence of genotoxic effects upon human lymphocytes of SLMP53-1 appears to be dose-independent.

SLMP53-1 Exhibited Antitumor Properties In Vivo Xenograft Mouse Models

Currently, the toxicity and antitumor activity of SLMP53-1 are under study in vivo using xenograft mouse models. The preliminary results obtained showed that after four injections of 50 mg/kg of SLMP53-1, the growth of the HCT116 $p53^{+/+}$ tumors was considerably suppressed when compared to vehicle administration, without apparent effects on HCT116 $p53^{-/-}$ tumors. Because p53-null tumors were not suppressed, it was confirmed that SLMP53-1 inhibited the tumor growth in a wt p53-dependent manner.

All the studies herein presented for SLMP53-1 are underway for SLMP53-2.

As the majority of mutant p53 reactivating compounds, such as CP-31398, WR-1065 and P53R3 (Wang and Sun, Translational Oncology 2010, 3:1-12), SLMP53-1 activates wt p53 present in no malignant cells. However, more potent and selective activators of mutant p53 forms may be obtained from derivatization of compound SLMP53-1.

Application

As such, besides the potential use of SLMP53-1 as molecular probe and possible anticancer agent, SLMP53-1 mainly represents a useful lead compound for the structure-based design of more potent and selective activators of mutant p53 forms.

Alternatively, with the emerging concept of cyclotherapy, wt p53 activators, as SLMP53-1, may function as chemoprotectants in normal tissues when combined with conventional chemotherapeutic drugs in patients with p53-defective tumors (through selective induction of p53-dependent G1- and/or G2-phase cell cycle arrest in normal tissues while leaving cancer cells lacking functional p53 vulnerable to subsequent treatment with S- or M-phase poisons) (Chen et al. Biochem Pharmacol. 2010, 80:724-30; Wang and Sun, Translational Oncology 2010, 3:1-12; van Leeuwen Cell Cycle 2011, 10:1590-1598).

As a whole, our finding therefore adds, for the first time, the tryptophanol-derived oxazoloisoindolinone scaffold to the list of chemotypes p53 activators.

A formulation or pharmaceutical composition containing these compounds as effective components, together with pharmaceutically effective carriers, may be used in the treatment of cancers with wt or mutant p53, after further pre-clinic studies.

In a preferred embodiment, the pharmaceutical composition comprises a pharmaceutically acceptable vehicle and a therapeutically active amount the compound of the present invention or its isomers, salts or esters.

The composition may be administered via topical, oral, parenteral or injectable route.

Such composition may further comprise a chemotherapeutic agent.

Naturally, the present embodiments are not in any way limited to the embodiments described in this document and a person with average knowledge in the field will be able to predict many possible changes to it without deviating from the main idea, as described in the claims.

The invention claimed is:

1. A compound or pharmaceutically acceptable salt, ester, solvate or prodrug thereof, of formula (I):

wherein:
X is C=O, CH$_2$, CH—OH, C=NOH, C=NOCH$_3$, NO, NOH, S=O or SO$_2$;
R$^1$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, substituted or unsubstituted aryl, substituted or unsubstituted heteroaryl, substituted or unsubstituted aralkyl, or substituted or unsubstituted heteroaralkyl;
R$^2$ is independently selected from the group consisting of hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkoxy, hydroxyl, aldehyde, halogen, trifluoromethyl, carboxyl, cyano, nitro, carbonylmethylsulfone, trifluoromethylsulfone, and substituted or unsubstituted sulfonamide, substituted or unsubstituted aryl, substituted or unsubstituted heteroaryl, substituted or unsubstituted aralkyl, or substituted or unsubstituted heteroaralkyl;

$R^3$ to $R^9$ are independently selected from the group consisting of hydrogen, substituted or unsubstituted alkyl, substituted or unsubstituted cycloalkyl, substituted or unsubstituted heterocyclyl, substituted or unsubstituted hydroxyalkyl, substituted or unsubstituted alkenyl, substituted or unsubstituted alkynyl, substituted or unsubstituted alkylamine, substituted or unsubstituted alkoxy, hydroxyl, aldehyde, halogen, trifluoromethyl, amine, carboxyl, cyano, nitro, carbonylmethylsulfone, trifluoromethylsulfone, and substituted or unsubstituted sulfonamide, substituted or unsubstituted aryl, substituted or unsubstituted heteroaryl, substituted or unsubstituted aralkyl, or substituted or unsubstituted heteroaralkyl;

$R^{10}$ is hydrogen, substituted or unsubstituted alkyl, substituted or unsubstituted cycloalkyl, substituted or unsubstituted heterocyclyl, substituted or unsubstituted hydroxyalkyl, substituted or unsubstituted alkylamine, substituted or unsubstituted alkenyl, substituted or unsubstituted alkynyl, substituted or unsubstituted aryl, substituted or unsubstituted heteroaryl, substituted or unsubstituted aralkyl, or substituted or unsubstituted heteroaralkyl.

2. The compound according to claim 1, wherein the compound comprises one or more asymmetric centers such as enantiomer, diastereomer or other stereoisomeric forms defined in terms of absolute stereochemistry as (R)- or (S)- or as (D)- or (L)-, its tautomer or racemate; or mixture thereof, or pharmaceutically acceptable salt, ester, solvate or prodrug thereof.

3. A compound according to claim 1, wherein at least one of
$R^1$ is a substituted or unsubstituted alkylamine;
$R^3$ to $R^9$ are, independently of each other, an amine or a substituted or unsubstituted alkylamine, and
wherein the compound comprises counterions selected from the group consisting of $HCO_3^-$, $CO_3^{2-}$, $Cl^-$, $NH_2C_6H_4SO_3^-$, and $1\text{-}CH_3C_6H_2\text{-}3\text{-}OH\text{-}4(CHCH_3)\text{-}6\text{-}SO_3^-$ which are coordinated or ionically bound in the amine or alkylamine.

4. A compound according to claim 1, wherein the compound is of formula (II)

(II)

5. A compound according to claim 1, wherein in the compound is of formula (III)

(III)

6. A pharmaceutical composition comprising a therapeutically effective amount of the compound described in claim 1 and further comprising a pharmaceutically effective carrier.

7. A pharmaceutical composition according to claim 6, further comprising a chemotherapeutic agent.

8. A pharmaceutical composition according to claim 6, wherein it is administered via topical, oral, parenteral or injectable route.

9. A method for treating breast cancer that is positively influenced by the activation of wild-type or mutant p53 forms comprising administering the the pharmaceutical composition of claim 6 to a mammal in need thereof.

10. A method for treating breast cancer that is positively influenced by the activation of wild-type or mutant p53 forms comprising administering the compound of claim 2 to a mammal in need thereof.

11. A method for treating colon cancer that is positively influenced by the activation of wild-type or mutant p53 forms comprising administering the the pharmaceutical composition of claim 6 to a mammal in need thereof.

12. A method for treating colon cancer that is positively influenced by the activation of wild-type or mutant p53 forms comprising administering the compound of claim 2 to a mammal in need thereof.

* * * * *